(12) United States Patent
Brown et al.

(10) Patent No.: US 8,147,538 B2
(45) Date of Patent: *Apr. 3, 2012

(54) COVERED STENT

(75) Inventors: Brian J. Brown, Hanover, MN (US); Scott R. Smith, Chaska, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1115 days.

This patent is subject to a terminal disclaimer.

(21) Appl. No.: 12/014,178

(22) Filed: Jan. 15, 2008

(65) Prior Publication Data

US 2008/0114447 A1     May 15, 2008

Related U.S. Application Data

(62) Division of application No. 10/386,873, filed on Mar. 11, 2003, now Pat. No. 7,318,836.

(51) Int. Cl.
*A61F 2/06* (2006.01)
(52) U.S. Cl. ...................................................... 623/1.13
(58) Field of Classification Search .................. 623/1.11, 623/1.12, 1.13, 1.18, 1.32, 1.44; 606/191–198
See application file for complete search history.

(56) References Cited

U.S. PATENT DOCUMENTS

| 4,550,447 A | 11/1985 | Seiler, Jr. et al. |
| 5,024,671 A | 6/1991 | Tu et al. |
| 5,091,205 A | 2/1992 | Fan |
| 5,123,917 A | 6/1992 | Lee |
| 5,411,550 A | 5/1995 | Herweck et al. |
| 5,443,500 A | 8/1995 | Sigwart |
| 5,562,697 A | 10/1996 | Christiansen |
| 5,578,075 A | 11/1996 | Dayton |
| 5,591,197 A * | 1/1997 | Orth et al. ..................... 606/191 |
| 5,653,747 A | 8/1997 | Dereume |
| 5,693,085 A | 12/1997 | Buirge et al. |
| 5,697,967 A | 12/1997 | Dinh et al. |
| 5,700,285 A | 12/1997 | Myers et al. |
| 5,700,286 A | 12/1997 | Tartaglia et al. |
| 5,723,004 A | 3/1998 | Dereume et al. |
| 5,735,892 A | 4/1998 | Myers et al. |
| 5,749,880 A | 5/1998 | Banas et al. |
| 5,755,770 A | 5/1998 | Ravenscroft |
| 5,755,781 A * | 5/1998 | Jayaraman ................... 623/1.13 |
| 5,769,884 A | 6/1998 | Solovay |
| 5,788,626 A | 8/1998 | Thompson |

(Continued)

FOREIGN PATENT DOCUMENTS

EP    1 121 911    8/2001

(Continued)

OTHER PUBLICATIONS

PCT Notification Concerning Transmittal of International Preliminary Report on Patentability for International Application No. PCT/US2004/007099 (Chapter I of the Patent Cooperation Treaty) dated Sep. 29, 2005 (1 page).

(Continued)

*Primary Examiner* — Kevin T Truong
(74) *Attorney, Agent, or Firm* — Vidas, Arrett & Steinkraus

(57) ABSTRACT

A covered stent comprises a coiled sheet stent having at least a portion with open cell geometry and a graft material covering at least a portion of the coiled sheet stent.

18 Claims, 5 Drawing Sheets

U.S. PATENT DOCUMENTS

| | | |
|---|---|---|
| 5,824,046 A | 10/1998 | Smith et al. |
| 5,824,052 A | 10/1998 | Khosravi et al. |
| 5,824,054 A | 10/1998 | Khosravi et al. |
| 5,843,166 A | 12/1998 | Lentz et al. |
| 5,865,723 A | 2/1999 | Love |
| 5,922,393 A | 7/1999 | Jayaraman |
| 5,928,279 A | 7/1999 | Shannon et al. |
| 5,968,070 A | 10/1999 | Bley et al. |
| 5,993,489 A | 11/1999 | Lewis et al. |
| 6,001,125 A | 12/1999 | Golds et al. |
| 6,004,348 A | 12/1999 | Banas et al. |
| 6,010,529 A | 1/2000 | Herweck et al. |
| 6,048,360 A | 4/2000 | Khosravi et al. |
| 6,086,610 A | 7/2000 | Duerig et al. |
| 6,117,166 A | 9/2000 | Winston et al. |
| 6,139,573 A | 10/2000 | Sogard et al. |
| 6,165,211 A | 12/2000 | Thompson |
| 6,165,212 A | 12/2000 | Dereume et al. |
| 6,206,914 B1 | 3/2001 | Soykan et al. |
| 6,214,039 B1 | 4/2001 | Banas et al. |
| 6,245,099 B1 | 6/2001 | Edwin et al. |
| 6,270,524 B1 | 8/2001 | Kim |
| 6,290,722 B1 | 9/2001 | Wang |
| 6,312,463 B1 | 11/2001 | Rourke et al. |
| 6,325,820 B1 | 12/2001 | Khosravi et al. |
| 6,364,904 B1 | 4/2002 | Smith |
| 6,395,212 B1 | 5/2002 | Solem |
| 6,409,716 B1 | 6/2002 | Sahatjian et al. |
| 6,425,915 B1 | 7/2002 | Khosravi et al. |
| 6,468,300 B1 | 10/2002 | Freidberg |
| 6,475,232 B1 | 11/2002 | Babbs et al. |
| 6,475,234 B1 | 11/2002 | Richter et al. |
| 6,485,524 B2 | 11/2002 | Strecker |
| 6,537,310 B1 | 3/2003 | Palmaz et al. |
| 6,579,314 B1 | 6/2003 | Lombardi et al. |
| 6,673,102 B1 | 1/2004 | Vonesh et al. |
| 7,318,836 B2 * | 1/2008 | Brown et al. ............. 623/1.13 |
| 2002/0049490 A1 | 4/2002 | Pollock et al. |
| 2004/0181274 A1 | 9/2004 | Brown et al. |

FOREIGN PATENT DOCUMENTS

| | | |
|---|---|---|
| EP | 1157674 | 7/2005 |
| WO | 99/48441 | 9/1999 |
| WO | 01/01885 | 1/2001 |
| WO | 01/58384 | 8/2001 |

OTHER PUBLICATIONS

PCT International Preliminary Report on Patentability for International Application No. PCT/US2004/007099 dated Sep. 16, 2005 (6 pages).

PCT Notification of Transmittal of the International Search Report and the Written Opinion of the International Searching Authority, or the Declaration for International Application No. PCT/US2004/007099 dated Jul. 28, 2004 (3 pages).

PCT International Search Report for International Application No. PCT/US2004/007099 dated Jul. 28, 2004 (4 pages).

PCT Written Opinion of the International Searching Authority for International Application No. PCT/US2004/007099 dated Jul. 28, 2004 (5 pages).

Communication Pursuant to Article 96(2) EPC for European Patent Application No. 04 718 536.8-2310 dated Jan. 5, 2007 (3 pages).

* cited by examiner

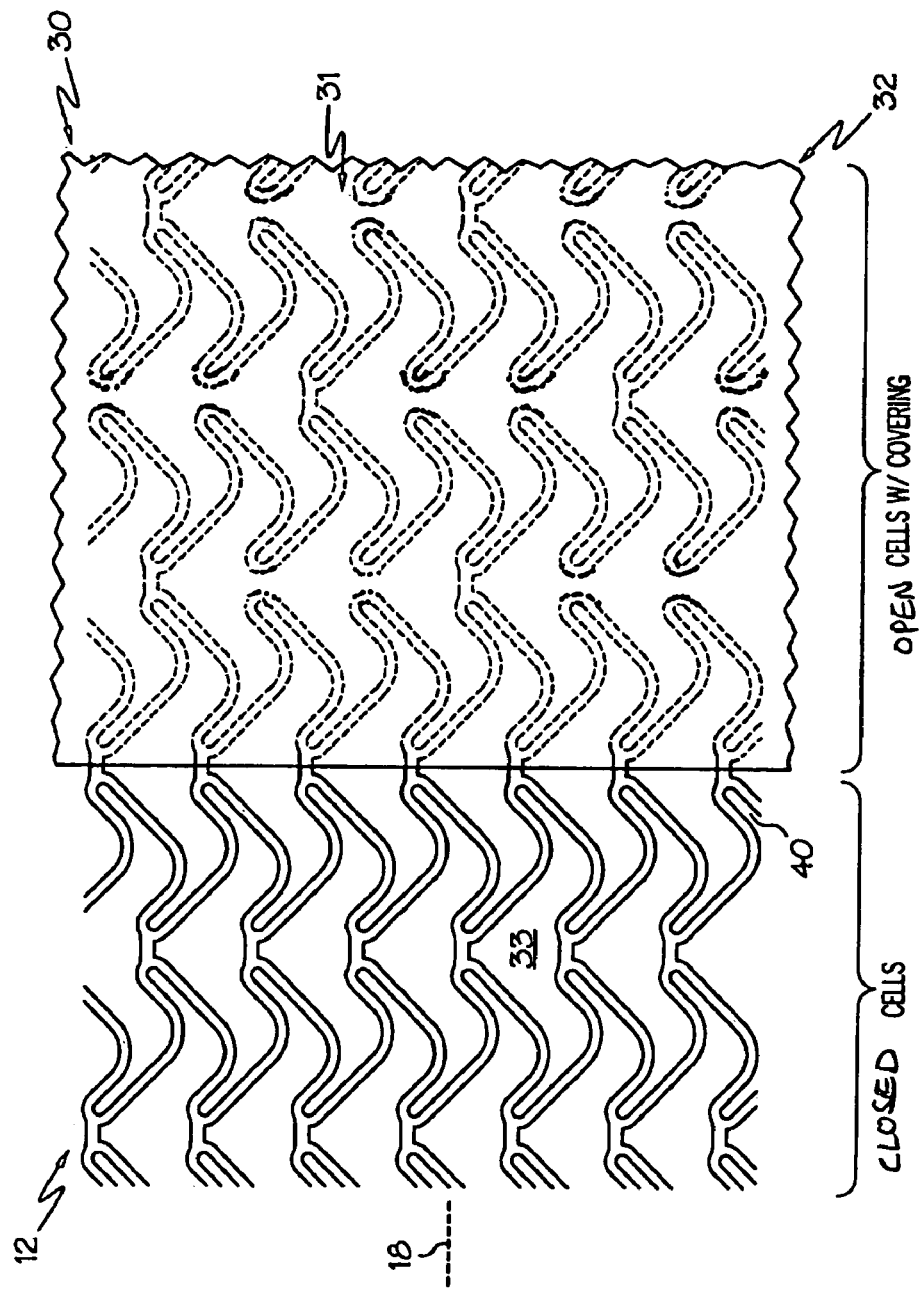

COVERED STENT

BACKGROUND OF THE INVENTION

The use of endoprostheses such as stents, stent-grafts, grafts, etc. is well known in maintaining the patency of bodily vessels and treating stenoses within arteries and other body spaces.

Stents can be constructed from tubes or sheets. Of those constructed from sheets, rolled and coiled, coiled sheet stents are known in the art. These coiled sheet stent designs have limited geometries to prevent tangling of the layers as the stent expands and un-coils. In general, the geometries of these coiled sheet stent designs are typically less flexible than the geometric stent designs available in other types of stents.

The coiled sheet stent designs typically have closed cell geometries in order to avoid tangling whereas some of the more flexible stents typically have open cell geometries. The closed cells typically have more connectors connecting adjacent portions of the coiled stent together than do the open cell geometries.

However, stent flexibility is very important in certain procedures due to the tortuous route the stent must make through the circulatory system in reaching the occlusion site. A concern with stents with "closed cell" geometries is that they will not be flexible enough to conform to the natural vessel curvature. A concern with stents with "open cell" geometries is the tangling of layers as the stent expands and uncoils at the site of the occlusion.

It would be desirable to introduce a flexible stent with "open cell" portions that do not experience tangling of the layers as the stent expands and uncoils into the occlusions area.

All U.S. patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the invention below.

A brief abstract of the technical disclosure in the specification is provided as well for the purposes of complying with 37 C.F.R. 1.72.

BRIEF SUMMARY OF THE INVENTION

The present invention is directed to a variety of embodiments, in at least one embodiment the invention is directed to the combination of a coiled sheet stent with graft material.

In at least one embodiment the graft material is applied as a single layer to one surface of the stent sheet.

In another embodiment the covering of graft material is applied as a single layer on each side of the stent sheet.

In another embodiment the stent sheet is placed inside a tubular graft material. The graft material is then pressed down onto the stent sheet. The tubular shape defined as any shape having a continuous cross section.

In another embodiment the stent sheet is laid onto one half of a graft material that is approximately twice as large as the stent sheet. The other half is then folded down to cover the other side of the stent sheet.

In at least one embodiment the graft material is placed over the entire stent sheet.

In another embodiment the graft material is placed over only a portion of the stent sheet.

In another embodiment the graft material is placed over several portions of the stent sheet.

In another embodiment the graft material delivers a drug.

In still another embodiment the stent sheet delivers a drug.

In at least one embodiment the graft material is selected from the group consisting of: ePTFE, Dacron/polyester, fibrin, collagen, and combinations thereof.

In yet another embodiment, the graft material serves as an electrical insulator between adjacent layers of the stent sheet.

In yet another embodiment, the invention is directed to a method of preventing radially adjacent cells of a coil stent from intertangling comprising the steps of providing a stent with a plurality of cells and disposing a graft material over at least some of the cells so that at least some cells which are radially adjacent one another are separated by the graft material, the graft material prevent tangling between adjacent layers of the stent. Typically, at least one of the radially adjacent cells will be of open cell geometry.

These and other embodiments which characterize the invention are pointed out with particularity in the claims annexed hereto and forming a part hereof. However, for a better understanding of the invention, its advantages and objectives obtained by its use, reference should be made to the drawings which form a further part

BRIEF DESCRIPTION OF THE SEVERAL VIEWS OF THE DRAWING(S)

A detailed description of the invention is hereafter described with specific reference being made to the drawings.

FIG. 2 is a flat view of a portion of a coiled sheet stent with both uncovered closed cell geometries and covered open cell geometries.

DETAILED DESCRIPTION OF THE INVENTION

Figure 1A:
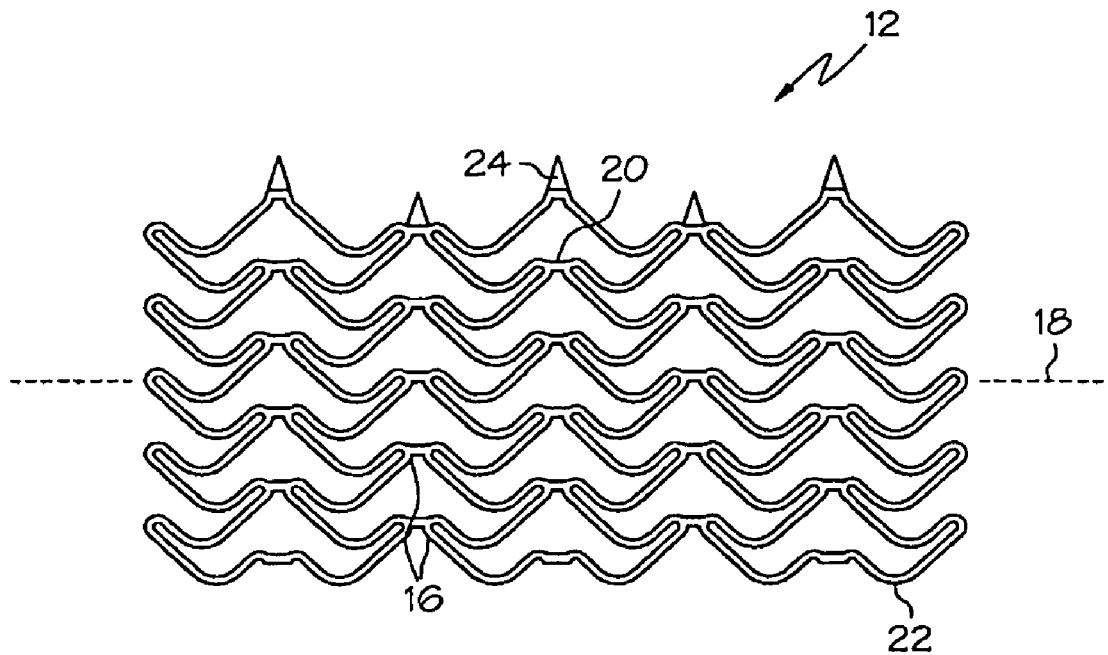
FIG. 1A is a flat view of a sheet stent having a closed cell geometry.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

As indicated above the present invention is directed to a variety of embodiments. In FIG. 1A a closed cell geometry of sheet stent 12 with longitudinal axis 18 is illustrated in that the number of interior peaks 16 is equal to twice the number of connectors 20. An open cell geometry has more interior peaks 16 than twice the number of connectors 20.

Figure 1B:
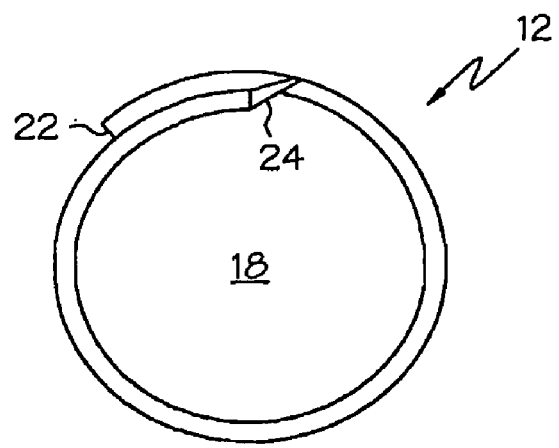
FIG. 1B is a cross-sectional perspective view of a coiled sheet tubular stent.

FIG. 1B is a cross-sectional view of a coiled sheet tubular stent 12 having a longitudinal axis 18. The outermost longitudinal edge 22 and the teeth 24 overlap when the stent sheet 12 is in a tubular form.

As shown in FIG. 2, in some embodiments the graft material 30 covers only a portion of sheet stent 12. In this figure the graft material 30 primarily covers a portion of the stent with open cell geometries 31 and leaves a portion of the closed cell geometries 33 uncovered. This gives the stent the flexibility of an open cell design without the tangling of layers that frequently occurs with open cell geometries; particularly with large cells, unconnected peaks within adjacent cell layers of cells may interfere with one another. The distal most edge 32 of the graft material 30 can also be a fold whereby the graft material 30 covers portions on both sides of the sheet stent 12.

Figure 3:
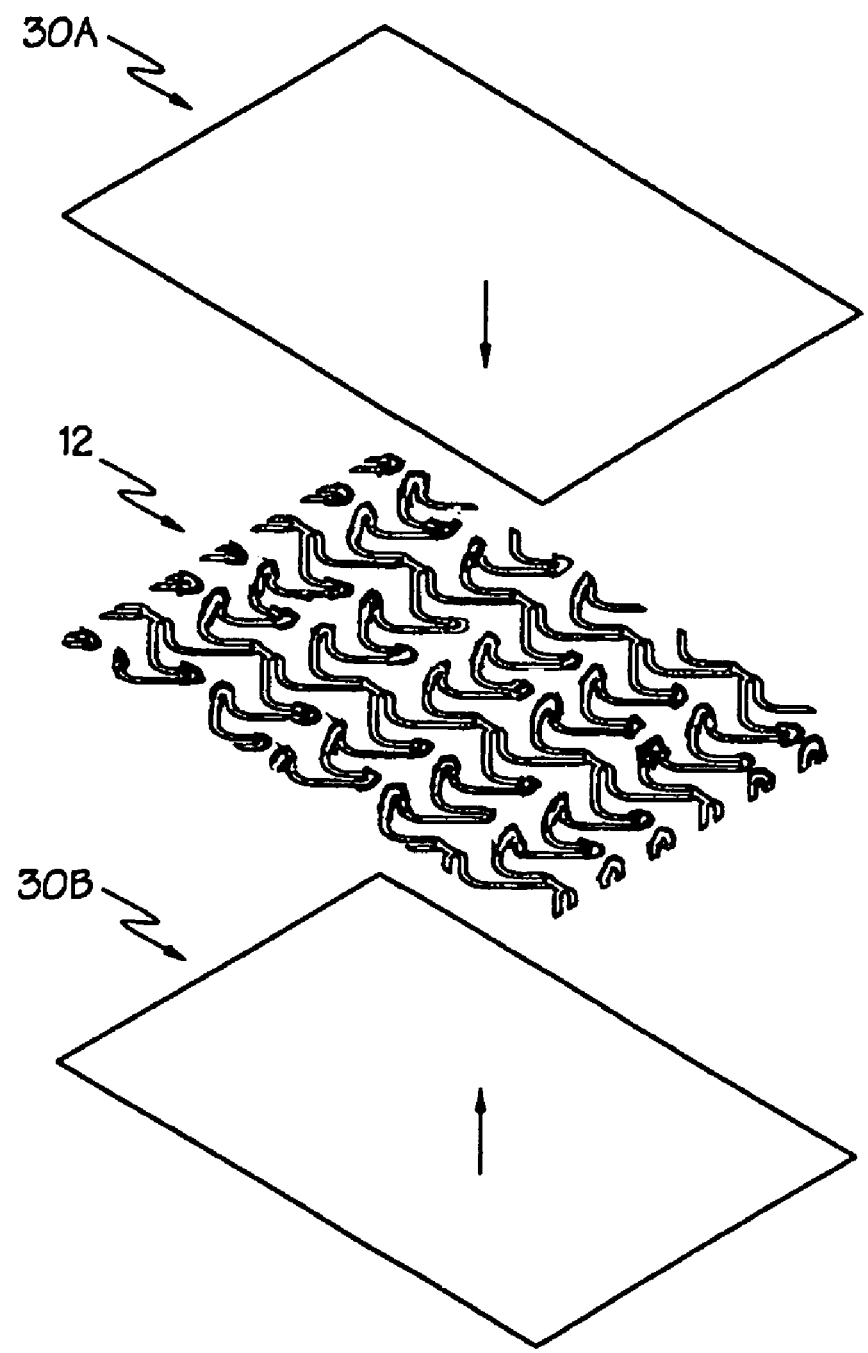
FIG. 3 is a perspective view of a sheet stent being pressed between two sheets of graft material, prior to being coiled.

As shown in FIG. 3, two graft materials 30A,30B are positioned to cover portions on both sides of sheet stent 12. Graft materials 30A,30B can be made of identical material or different materials. In some embodiments, graft material 30A does not match 30B in size and/or orientation. Hence some portion of graft 30A and graft 30B can contact one another without sheet stent 12 separating them. In some embodiments, the graft materials 30A,30B have no edges extending beyond the sheet stent 12. In other embodiments, only one or the other of the graft materials 30A,30B have edges which extend beyond the sheet stent 12. In other embodiments one graft material has an edge that extends beyond the sheet stent 12 and additionally folds over onto the other side of sheet stent 12 or folds over onto the other graft material that is in contact with the sheet stent 12.

Figure 4:
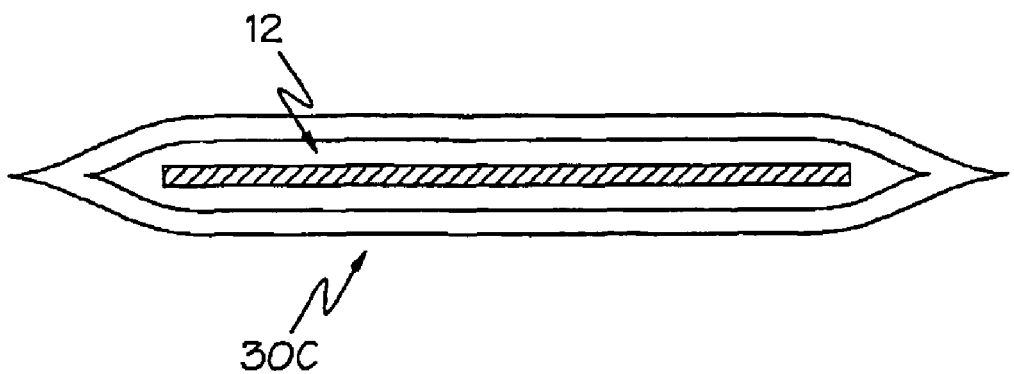
FIG. 4 is a cross-sectional view of a sheet stent inside a tubular graft material, prior to being coiled.

As shown in FIG. 4, sheet stent 12 is placed into tubular graft material 30C. Tubular graft material 30C is a continuous piece, but may contain different materials. Upon being placed in the tubular graft material 30C, graft material 30C is collapsed upon sheet stent 12. The tubular graft material 30 may or may not extend beyond the outside edges of the sheet stent in a latitudinal direction.

Figure 5:
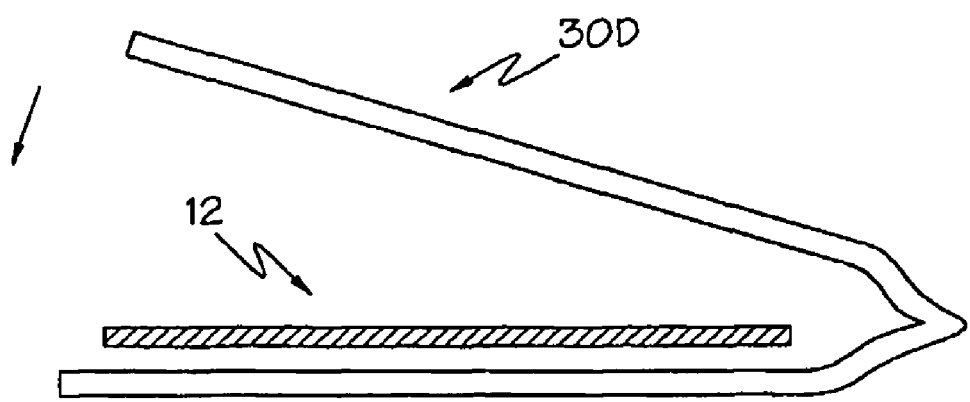
FIG. 5 is a cross-sectional view of a sheet stent being folded inside a single sheet of tubular graft material, prior to being coiled.

As shown in FIG. 5, sheet stent 12 is placed upon a graft material 30D that is approximately twice as long or wide as the sheet stent 12. The graft material 30D is then folded such that the sheet stent is between the two folded sides of the graft material 30D such that at least a portion of each side of the sheet stent 12 is covered with the graft material 30D. Sheet stent 12 may have both sides completely covered by graft material 30D or one side completely covered and the other side partially covered.

Figure 6:
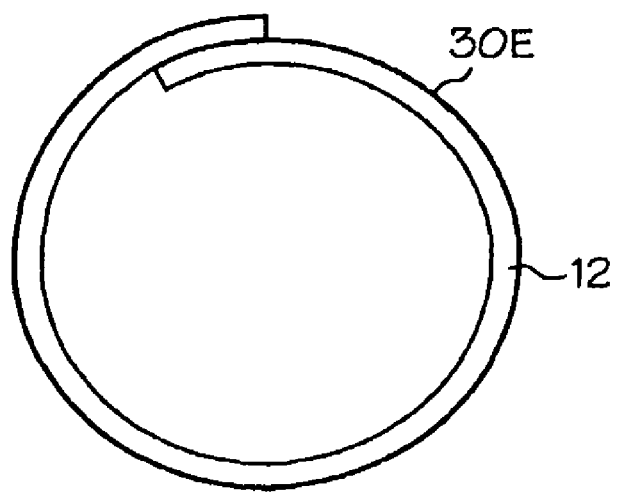
FIG. 6 is a cross-sectional view of a sheet stent showing a portion of the graft material between overlapping portions of the coiled sheet stent.
Figure 7:
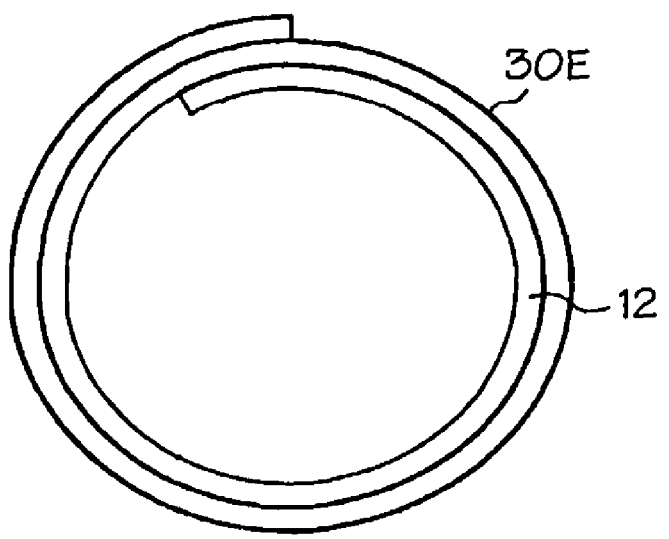
FIG. 7 is a cross-sectional view of a sheet stent showing multiple layers of the graft material between overlapping layers of the coiled sheet stent.

In FIG. 6 the graft material 30E is shown providing a layer between the portions of the sheet stent 12 which overlap. In FIG. 7 multiple layers of overlapping are shown wherein graft material 30E provides a layer between the radially overlapping portions of the sheet stent 12. It should be noted and evident from the disclosure that graft material may provide a layer between any adjacent portions of the sheet stent 12.

The graft material can also be selected so as to provide an electrical insulator layer between conductive layers of the stent or overlapping portions of the stent or both. This electrical insulator layer may be used to minimize or eliminate the formation of electrical disturbances (e.g. eddy currents) that might otherwise occur when using Magnetic Resonance Imaging (MRI) to image the stent or the body in which the stent is disposed. Such disturbances can interfere with Magnetic Resonance Imaging thereby reducing one's ability to visualize portions of the stent or the surrounding body (e.g. eddy currents may reduce the ability to visualize the interior of the stent).

As already indicated, this invention is applicable to self-expanding configurations of the stent sheet and mechanically expandable configurations of the stent sheet and to stent sheets made from a wide variety of materials, including both metal and plastic and any other material capable of functioning as an expandable stent. It may be thin-walled or thick walled. It may be of shape memory alloy such as Nitinol or the like, etc or of stainless steel, titanium or any other suitable, biocompatible metal as known in the art.

The inventive stents may also be provided with various bio-compatible coatings to enhance various properties of the stent. For example, the inventive stents may be provided with lubricious coatings. The inventive stents may also provide drug release over time. This release of drugs over time may be provided through drug-containing coatings, or direct implantation of a drug onto or into the graft, or drug-containing coatings applied prior to applying the graft material. The graft material may also be used to deliver a drug.

The inventive stents may also be provided with a sugar or more generally a carbohydrate and/or a gelatin to maintain the stent on a balloon during delivery of the stent to a desired bodily location. Other suitable compounds for treating the stent include biodegradable polymers and polymers which are dissolvable in bodily fluids. Portions of the interior and/or exterior of the stent may be coated or impregnated with the compound. Mechanical retention devices may also be used to maintain the stent on the balloon or delivery catheter during delivery. To that end, the use of other coatings on the inventive stents is also within the scope of the invention.

The coating may comprise one or more non-genetic therapeutic agents, genetic materials and cells and combinations thereof as well as other polymeric coatings.

Non-genetic therapeutic agents include anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anticoagulants such as D-Phe-Pro-Arg chloromethyl keton, an RGD peptide-containing compound, heparin, antithrombin compounds, platelet receptor antagonists, antithrombin anticodies, anti-platelet receptor antibodies, aspirin, prostaglandin inhibitors, platelet inhibitors and tick antiplatelet peptides; vascular cell growth promotors such as growth factor inhibitors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vascoactive mechanisms.

Genetic materials include anti-sense DNA and RNA, DNA coding for, anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor .alpha. and .beta., platelet-derived endothelial growth factor, platelet-derived growth factor, tumor necrosis factor .alpha., hepatocyte growth factor and insulin like growth factor, cell cycle inhibitors including CD inhibitors, thymidine kinase ("TK") and other agents useful for interfering with cell proliferation the family of bone morphogenic proteins ("BMP's"), BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Desirable BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

Cells can be of human origin (autologous or allogeneic) or from an animal source (xenogeneic), genetically engineered if desired to deliver proteins of interest at the transplant site. The cells may be provided in a delivery media. The delivery media may be formulated as needed to maintain cell function and viability.

Suitable polymer coating materials include polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof, coatings from polymer dispersions such as polyurethane dispersions (for example, BAYHDROL®), fibrin, collagen and derivatives thereof, polysaccharides such as celluloses, starches, dextrans, alginates and derivatives, hyaluronic acid, squalene emulsions. Polyacrylic acid, available as HYDROPLUS® (Boston Scientific Corporation, Natick, Mass.), and described in U.S. Pat. No. 5,091,205, the disclosure of which is hereby incorporated herein by reference, is particularly desirable. Even more desirable is a copolymer of polylactic acid and polycaprolactone.

Other suitable coverings include nylon, collagen, PTFE and expanded PTFE, polyethylene terephthalate and KEVLAR, or any of the materials disclosed in U.S. Pat. Nos. 5,824,046 and 5,755,770. More generally, any known graft material may be used including synthetic polymers such as polyethylene, polypropylene, polyurethane, polyglycolic acid, polyesters, polyamides, their mixtures, blends and copolymers.

The stents may find use in coronary arteries, renal arteries, peripheral arteries including iliac arteries, arteries of the leg, aorta, arteries of the neck and cerebral arteries. The stents of the present invention, however, are not limited to use in the vascular system and may also be advantageously employed in other body structures, including but not limited to arteries, veins, biliary ducts, urethras, fallopian tubes, bronchial tubes, the trachea, the esophagus and the prostate. The inventive stent may be delivered on a catheter such as that discussed in WO 01/01885.

The stent sheets used in the inventive covered stents disclosed herein may be manufactured using any suitable known technique for manufacturing stent sheets including laser cutting or mechanically cutting a stent pattern in a sheet of material, etching, chemically or otherwise, a stent pattern in a sheet of material, or using an EDM (electrical discharge machining) technique to cut a stent pattern into a sheet of material.

The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

The invention claimed is:

1. A covered stent comprising:
a coiled sheet stent having a plurality of radially overlapping sections at least one of which includes an open cell geometry portion having a plurality of interior peaks, at least one of the interior peaks being disconnected from the other of the interior peaks, at least two of the interior peaks being connected to one another; and
a graft material covering at least a portion of the open cell geometry portion so that the graft material is between the radially overlapping sections to separate the at least one of the disconnected interior peaks from the radially overlapping sections.

2. The covered stent of claim 1, wherein the graft material covers the entire coiled sheet stent.

3. The covered stent of claim 1, wherein the graft material entirely covers only one side of the coiled sheet stent.

4. The covered stent of claim 1, wherein the graft material is located on an interior side and an exterior side of the coiled sheet stent.

5. The covered stent of claim 4, wherein the graft material entirely covers the interior side of the coiled sheet stent and less than the entirety of the exterior side of the coiled sheet stent.

6. The covered stent of claim 4, wherein the graft material entirely covers an exterior side of the coiled sheet stent and less than the entirety of the interior side of the coiled sheet stent.

7. The covered stent of claim 1, wherein the graft material is tubular and the stent is placed inside the graft material such that a portion of a first and a portion of a second side are covered.

8. The covered stent of claim 1, wherein there is a plurality of layers with graft material between multiple layers.

9. The covered stent of claim 8, wherein the graft material is constructed of MRI compatible material.

10. The covered stent of claim 8 wherein the graft material acts as an electrical insulator between conductive layers of the stent.

11. The covered stent of claim 1, having the graft material between cells which are radially adjacent.

12. The covered stent of claim 1, wherein the graft material comprises a sleeve in which the sheet stent is located.

13. The covered stent of claim 12, wherein the sleeve has an outside edge beyond which the sheet stent extends.

14. The covered stent of claim 12, wherein the sleeve has outside edges beyond which the sheet stent extends in a latitudinal direction.

15. The covered stent of claim 1, wherein the sheet stent has opposite sides and an edge from which the sides extend, the graft material comprising a sheet structure covering at least portions of the sides and edge such that the sheet structure extends continuously from one of the sides across the edge to the other of the sides.

16. The covered stent of claim 15, wherein the edge defines a first edge, the sheet structure having a second edge, the sheet structure having respective portions which face corresponding sides of the sheet stent, the respective portions of the sheet structure extending beyond the second edge.

17. A method for making a covered stent comprising:
providing a sheet stent at least a section of which includes an open cell geometry portion having a plurality of interior peaks, at least one of the interior peaks being disconnected from the other of the interior peaks, at least two of the interior peaks being connected to one another;
providing a graft material having a sleeve including an interior region and at least one edge which is open;
inserting the sheet stent into the interior region of the sleeve;
collapsing the sleeve upon the sheet stent to cover the open cell geometry portion; and
coiling the sheet stent such that sections thereof radially overlap wherein at least one of the radially overlapping sections includes the open cell geometry portion;
the coiling providing for the graft material to be located between the radially overlapping sections to separate the at least one of the disconnected interior peaks from the radially overlapping sections.

18. A method for making a covered stent comprising:
providing a sheet stent at least a section of which includes an open cell geometry portion having a plurality of interior peaks, at least one of the interior peaks being disconnected from the other of the interior peaks, at least two of the interior peaks being connected to one another, the sheet stent having opposite sides and an edge from which the sides extend;
providing a graft material having a sheet structure;
locating the sheet structure to face one or more of the edge and opposite sides of the sheet stent;
folding the sheet structure around the sheet stent to cover the edge and opposite sides thereof wherein the open cell geometry portion is covered by the sheet structure; and
coiling the sheet stent such that sections thereof radially overlap wherein at least one of the radially overlapping sections includes the open cell geometry portion,
the coiling providing for the graft material to be located between the radially overlapping sections to separate the at least one of the disconnected interior peaks from the radially overlapping sections.

\* \* \* \* \*